(12) United States Patent
Helgeson

(10) Patent No.: US 8,915,215 B1
(45) Date of Patent: Dec. 23, 2014

(54) METHOD AND APPARATUS FOR MONITORING POULTRY IN BARNS

(71) Applicant: Scott A. Helgeson, Bloomington, MN (US)

(72) Inventor: Scott A. Helgeson, Bloomington, MN (US)

(*) Notice: Subject to any disclaimer, the term of this patent is extended or adjusted under 35 U.S.C. 154(b) by 66 days.

(21) Appl. No.: 13/986,893

(22) Filed: Jun. 17, 2013

Related U.S. Application Data

(60) Provisional application No. 61/690,169, filed on Jun. 21, 2012.

(51) Int. Cl.
*A01K 29/00* (2006.01)

(52) U.S. Cl.
USPC .......................................... 119/421; 119/437

(58) Field of Classification Search
USPC .................................. 119/421, 436, 437, 174
See application file for complete search history.

(56) References Cited

U.S. PATENT DOCUMENTS

| | | | | |
|---|---|---|---|---|
| 5,452,364 A | * | 9/1995 | Bonham | 381/92 |
| 5,492,082 A | * | 2/1996 | Krevinghaus et al. | 119/448 |
| 5,893,057 A | * | 4/1999 | Fujimoto et al. | 704/246 |
| 6,535,131 B1 | * | 3/2003 | Bar-Shalom et al. | 340/573.1 |
| 7,065,416 B2 | * | 6/2006 | Weare et al. | 700/94 |
| 7,454,334 B2 | * | 11/2008 | Agranat | 704/231 |
| 7,963,254 B2 | * | 6/2011 | Patton | 119/712 |
| 8,223,980 B2 | * | 7/2012 | Dooling et al. | 381/56 |
| 8,838,260 B2 | * | 9/2014 | Pachet et al. | 700/94 |
| 2003/0125946 A1 | * | 7/2003 | Hsu | 704/246 |
| 2004/0107104 A1 | * | 6/2004 | Schaphorst | 704/270 |
| 2004/0150528 A1 | * | 8/2004 | Natividade et al. | 340/573.3 |
| 2005/0254663 A1 | * | 11/2005 | Raptopoulos et al. | 381/71.1 |
| 2005/0281410 A1 | * | 12/2005 | Grosvenor et al. | 381/61 |
| 2006/0256973 A1 | * | 11/2006 | Kirsten et al. | 381/61 |
| 2006/0277037 A1 | * | 12/2006 | Woodcock et al. | 704/208 |

* cited by examiner

*Primary Examiner* — Yvonne Abbott

(74) *Attorney, Agent, or Firm* — Richard John Bartz

(57) ABSTRACT

A method and apparatus for monitoring and acquiring data concerning the health of poultry and animals housed in one or more barns or enclosed environments predicated upon the frequencies and intensity of sounds generated by the poultry and animals to obtain baseline data of healthy and happy poultry and animals.

16 Claims, 3 Drawing Sheets

METHOD AND APPARATUS FOR MONITORING POULTRY IN BARNS

CROSS REFERENCE TO RELATED APPLICATION

This application claims the priority of U.S. Provisional Application Ser. No. 61/690,169 filed Jun. 21, 2012.

FIELD OF THE INVENTION

The invention relates to monitoring and managing environmental variables and poultry conditions of poultry located in one or more barns to create forecasting data for marketing and to maximize poultry health.

BACKGROUND OF THE INVENTION

Modern day poultry producers have investigated almost every avenue to obtain greater efficiency and maximum yield. Most of these techniques rely on past data to signal where problems occurred and then try to determine cause. This accounting approach has serious limitations in figuring out what and how poultry either thrive or become unhealthy, or dead. Clearly post data cannot proactively manage a healthy poultry flock. Real-time predictive information is necessary to monitor and take corrective action. While sophisticated barn and poultry flock monitoring systems exist and allow real-time monitoring, there is not yet an attempt to gather and correlate multiple monitoring inputs into a predictive statistical model. To be successful, such a model needs a baseline indicator of poultry stress and the ability to correlate multiple streams of environmental data to changes in the baseline.

Modern poultry barns often incorporate centralized monitoring and control systems that allow for control and monitoring the following:
  Feed consumption
  Water consumption
  Lighting schedule
  Temperature inside and out
  Humidity inside and out
  Fan operation Information from these types of systems are typically available as historical after-the-fact batch downloads, sometimes weeks later, as in accounting systems, as well as state-of-the art real-time monitoring and warning systems, some using a personal computer, smart phone or an internet interface. From this data, environmental anomalies, such as extreme temperatures can be monitored via warning indicators to allow evasive actions to mitigate or avoid fatal environmental stresses to the poultry flock. These systems are successful in monitoring single variables, such as temperature and humidity that can avert potential losses if acted upon quickly. Examples of methods and systems for managing and operating poultry barns are disclosed in U.S. Pat. Nos. 4,700,887; 7,751,942 and 7,904,284.

While these systems are useful, they are limited. Because of the geographical isolation and distribution of poultry barns, there are real barriers to collecting data from multiple locations simultaneously. Additionally, there is the limit to how much data can be collected and stored using traditional information systems technology of centralized processing. Typically, because of low margins inherent in running a poultry business, accounting and information services are most focused on and concerned with transaction efficiencies, running the business and have little time or resources devoted to creating a centralized monitoring system for their barn network. Without a method to consolidate environmental data, predictive correlation modeling is impossible.

SUMMARY OF THE INVENTION

The invention proceeds from simple monitoring to the level of sophisticated analysis of discreet environmental variables against background poultry sounds. The expected outcome of a proactive model uses established statistical methodologies to identify multiple predictive relationships within the different types of environmental data against the baseline, poultry sounds. The goal is to create a valuable forecasting tool for marketing, to predict weeks in advance the ending weight of the poultry flock, as well as modifying environmental controls, such as fans, light, and feed to maximizing poultry health. Specifically, the technique is built around measuring correlating, and monitoring the sounds poultry make as baseline of health. Environmental factors that can impact health, such as humidity, heat, ammonia, etc., will first show as a stressor to poultry and is directly demonstrated by changes in sound volumes and pitch. For example, if the baseline sound shows a high level of beginning stress, and one factor is on the increase, such as humidity, overall stress could lead to sudden poultry mortality. Knowing this in advance could enable the grower to make proactive changes in the environment, from changes in lighting, to increased ventilation, to reduced feeding. On the other hand, if overall stress is within normal range, a solitary increase in one stressor may not be enough to cause concern. This reliable indicator of poultry flock stress can be linked to warning indicators via smart devices, signaling growers to adjust environmental variables before stress levels became lethal.

Cloud computing is a general term that describes the current trend to store and process information independent of local physical infrastructure. Cloud services are varied but can provide a flexible, pay-as-you need, location-independent secure, and distributed service as a promising alternative to traditional information service hardware and software. As the cost of storage has exponentially gone down, cloud services now have the capacity to store vast amounts of data in a centralized database that is easily scalable. Thus, a system may be rolled out from a test to multiple locations without any restrictions in lead-time that exists in the traditional paradigm.

The method of the invention relies on bypassing traditional transaction databases and transmitting information from many geographical locations into one relational cloud database. This database is accessible through an Internet connection to any browser or smart device with the proper sign-on credential. This central database also allows for the creation of complex queries to analyze the large amount of diverse data from single to multiple of locations. These SQL queries are the key access point into discovering relationships among disparate and discrete environmental data that is being collected in real time at the barn and poultry flock level. Using the SQL query, researchers can study data that may have a complex predictive relationships with other data. These correlations between different types of environmental data can be validated using statistical methodology. From these relationships, proactive warning systems can be built to alert growers and management of significant changes in poultry flock health. Additionally, the centralize data will enable better forecasting of ending poultry flock weight and poultry characteristics—information valuable to marketing and matching supply to customer demand.

A range of environmental and poultry parameters can be monitored in real time or sequentially at set intervals to provide data with regard to stress of the poultry and health of the poultry flock. These parameters include:

Temperature with the poultry barn,
Temperature outside of the poultry barn,
Humidity of the air in the poultry barn;
On or off lighting in the poultry barn;
Operation of air ventilating fans;
Water consumption of the poultry flock;
Poultry weight in real time or at intervals;
Feed consumption of poultry flock;
Ammonia concentrations;
Dust and particle counts;
Poultry movement;
Poultry concentrations;
Decibel levels of poultry noise to indicate poultry stress;
Frequency changes of poultry noise to indicate stress;
Infrared monitoring; and
Video monitoring.

The key challenge is to find one or more variables that can stand alone as baseline indicators of health. The sounds that individual birds make can collectively indicate the state of poultry welfare, or chicken "happiness". Changes in overall decibel levels measured against frequency can profile different states of poultry welfare. Once this is done, other variables can be correlated against the baseline to create a multidimensional model with predictive capabilities. Carefully measuring sounds from the poultry flock provides the key link to making sense of all the other variables. Sounds would be measured in 2 to 5 locations within a poultry barn to access overall and localized changes. If necessary, noise-cancelling filters can be used to isolate poultry flock noise from mechanical sounds from fans and other machinery. Real-time monitoring of noise is the key indicator as to whether the poultry flock is "happy" or stressed and to what degree.

Just as with humans, the sounds poultry make are complex in nature and it is sometimes difficult to decipher the meaning. But sounds that a bird will make are a form of communication to other birds, as a sign of contentment, territorial signaling, and warning. Sounds can also indicate extreme agitation and stress. Measuring changes in sound against a baseline of "normal contentment" gives a strong warning signal of trouble, unless the factors causing the stress are mitigated.

The method of the invention includes the measurement of the sounds that poultry are making in real time. Along with monitoring of other environmental indicators, changes in the poultry flock sounds can be highly predictive when combined with information about other changes in the environment. The poultry sounds in the barn can be a treasure of information when combined with other data. Used correctly, this real-time data can be used to maximize the health of the poultry flock, doing whatever can be helpful by the grower to make the life of a bird as "happy" as possible.

DESCRIPTION OF THE INVENTION

Figure 1:
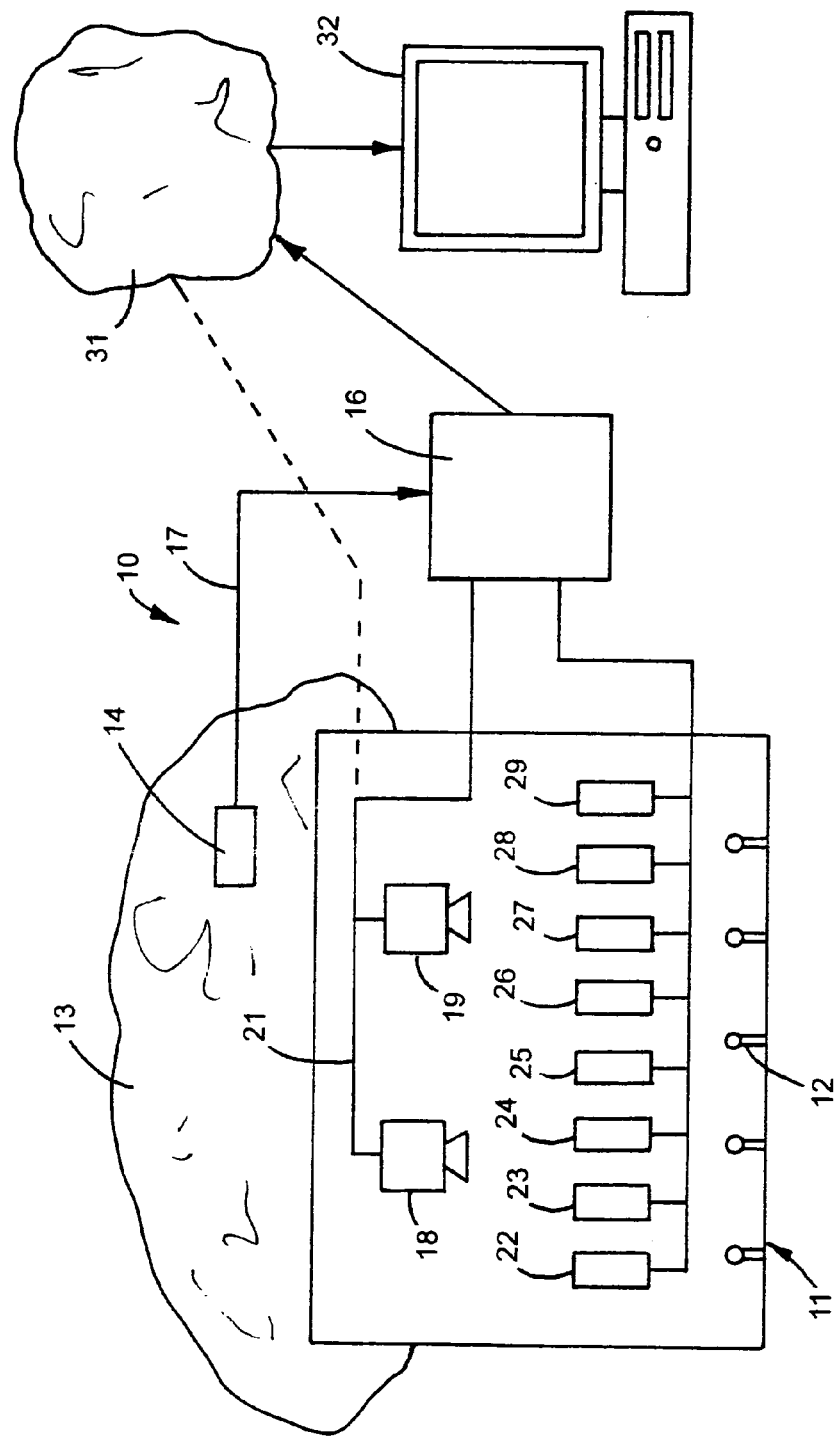
FIG. 1 is a diagrammatic view of a poultry barn and baseline data system of the optimum health of the poultry in the barn.

The baseline data system 10 for collecting and storing data concerning a healthy flock of poultry is shown in FIG. 1. A poultry barn 11 has an interior space accommodating a flock of poultry 12, such as broiler chickens. The environment 13 outside barn 11 is monitored with one or more sensors 14 to provide data regarding the temperature and relative humidity of the atmosphere and air movement or wind. The environment data sensed by sensor 14 is transferred to a data processor 16. A cable 17 wires sensor 14 to data processor 16. Sensor 14 can have wireless components that transfer data to data processor 16. Video and audio devices 18 and 19, such as video cameras and microphones, located within barn 11 monitor the time of day, the locations, concentrations and movements of the poultry 12 and the decibel level and frequencies of sounds generated by the poultry 12. One or more video devices can include infrared technology to monitor the poultry 12 in barn 11. The monitoring sequence can be continuous or at predetermined times.

A plurality of sensor devices 22 to 29 are located within barn 11. These sensor devices 22 to 29 monitor and generate data including but not limited to air temperature, air humidity, dust concentration in barn 11, water consumption of the poultry, operation of one or more air movers, such as fans that regulate the flow of air within barn 11, feed consumption of the poultry and the ammonia concentration of the air in the barn 11.

Data processor 16 includes a data memory or a look-up table that provides baseline data of a healthy flock of poultry 12 in barn 11. The audio data of decibel levels and frequencies of the sounds generated by the poultry 12 can be used as baseline data. Deviations of the decibel levels and frequencies of the sounds generated by the poultry 12 will trigger the comparison of real-time environment data and data from sensing devices 22-29 with the baseline data. Deviations from the baseline data provide information as to the causes of environment and barn conditions that relate to the unhealthy poultry. The poultry manager can adjust the barn environment to mitigate the adverse conditions based upon the baseline data deviations.

Figure 2:
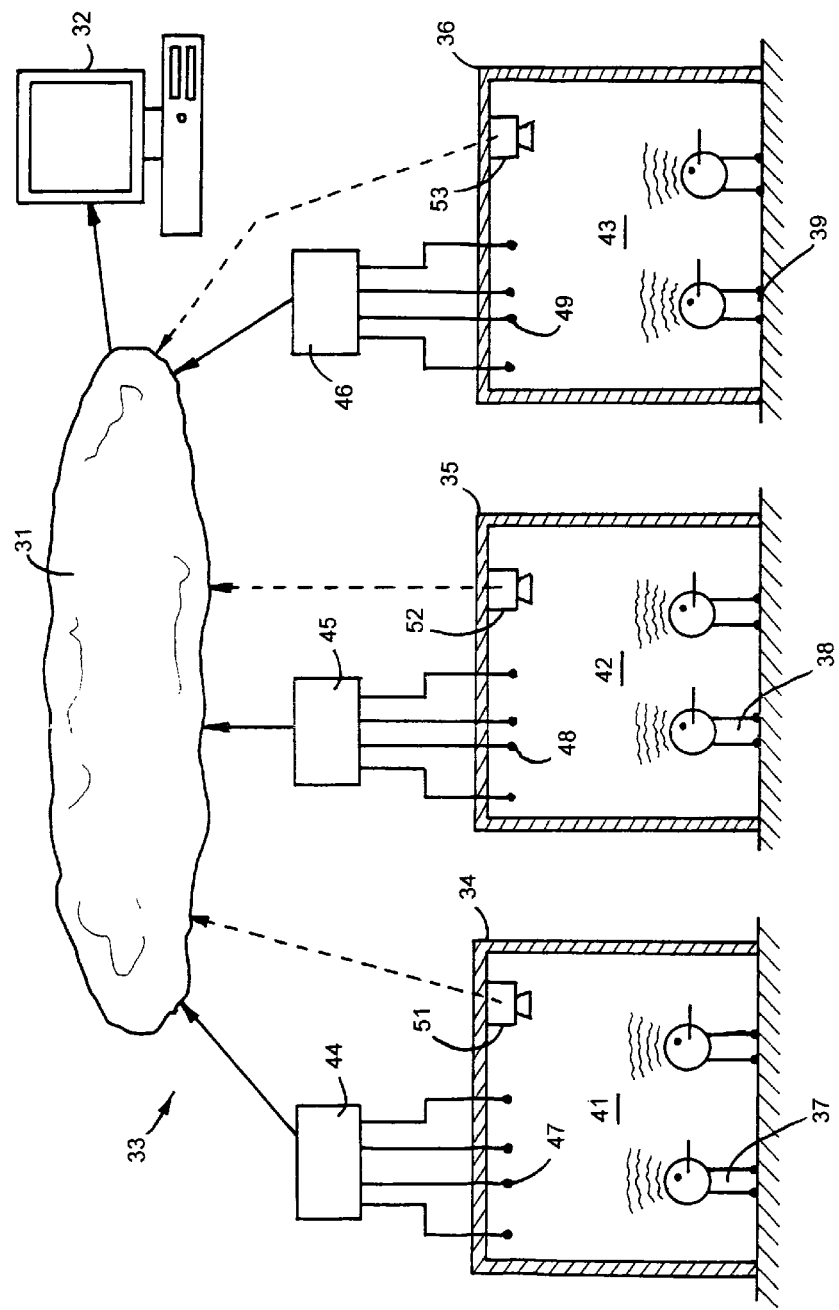
FIG. 2 is a diagrammatic view of a plurality of poultry barns associated with the apparatus and method for monitoring the environment and poultry in the barns.

An environment and poultry monitoring system 33, shown in FIG. 2, monitors the stress of the poultry and environment conditions in a plurality of poultry barns 34, 35 and 36. The barns 34-36 accommodate poultry flocks 37, 38 and 39 located within interior rooms or free spaces 41, 42 and 43. Data processors 44, 45 and 46 wired to sensors 47, 48 and 49 located in aviary rooms 41, 42 and 43 collect environment conditions, food and water supplies, fan operations and lighting conditions within the rooms. Video and audio devices 51, 52 and 53, such as video cameras and microphones, record poultry flock movement and concentrations and sense sound frequencies and decibel or intensity of sounds generated by the poultry flock. The environment data, food and water consumption data, lighting and fan operation acquired by data processors 44, 45 and 46 are transferred to cloud 31 and stored along with the baseline data. Data processor 32 is operable to access the data including baseline data from the cloud 31 to monitor the poultry flock in each room 41, 42 and 43 separately or in combination. The operator can make real-time adjustments to the environment, feed and water or lighting to remedy adverse conditions the effect the well-being of the poultry flock. The term poultry includes chickens, ducks, turkeys and other types of avian creatures.

Figure 3:
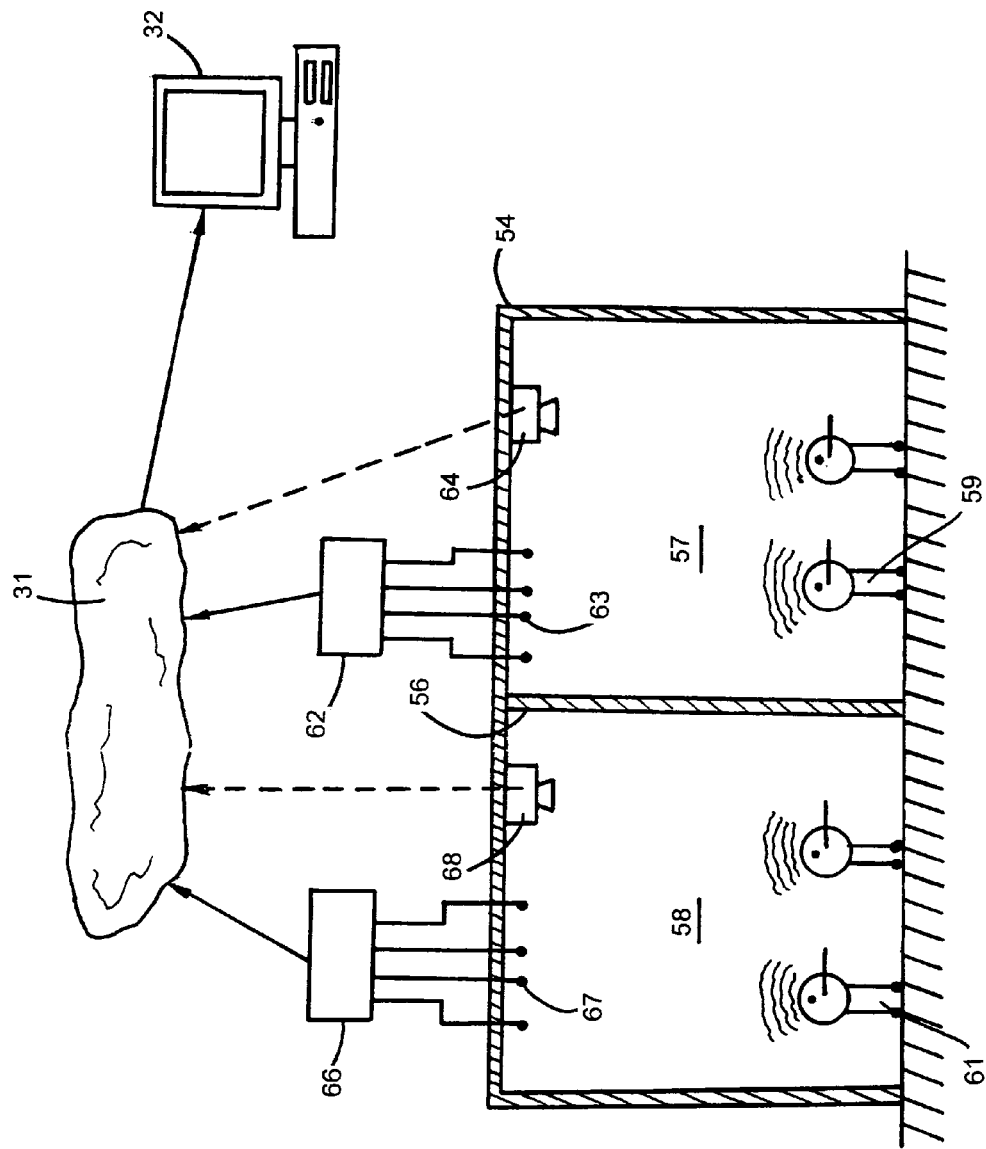
FIG. 3 is a diagrammatic view of a poultry barn divided into a brooder section and a broiler section associated with the apparatus and method for monitoring the environment and poultry in each section.

Poultry chicks during the first three weeks of life are not able to control their own body temperature. Heaters in brooding sections of poultry barns are used to maintain the air temperature in the range of 85°-95° F. After about 20 to 21 days, the chicks are able to regulate their body temperature without the use of the heaters. A poultry barn 54, shown in FIG. 3, has an interior room divided with a partition 56 into a brooder aviary space 57, and a broiler aviary space 58 to provide a grow-out period for the poultry. Chicks 59 are located in brooder space 57. More mature poultry 61 are located in broiler space 58. A first data processor 62 wired to sensors 67 located within brooder space 57 monitors the environment within brooder space and controls the air temperature therein. Data processor 62 also monitors chick movements and sounds. A video camera and audio microphone 64 monitors chick movements and concentrations and sounds generated by the chicks. The data acquired by data processor 62 is transferred to cloud 31 and stored therein along with baseline data. Data processor 32 is operable to access the data in the cloud 31 along with the baseline data and utilize this data to monitor and control chick health and remedy adverse condition, that are detrimental to the well-being of the chicks.

A second data processor 66 wired to a plurality of sensor devices 67 located in broiler space 58 monitors the environmental and poultry conditions in broiler space 58 of poultry barn 54. The collected data is transferred by data processor 66 to cloud 31. The sensor devices 67 are the same as sensor devices 22 to 29 shown in FIG. 1. These sensor devices monitor and generate data including but not limited to air temperature, air humidity, dust concentration, fan operation, lighting conditions, and ammonia concentrations of the air in the barn. A video and audio device 68, such as a video camera and microphone, located in broiler section 58 of barn 54 monitors movements and concentrations of poultry and the frequencies and intensity of sounds generated by the poultry flock 61. A plurality of video and audio devices can be used to monitor and acquire video and sounds of the poultry flock 61 in different locations in broiler space 58 of barn 54. The data acquired by the video and audio device 68 is transferred to cloud 31 and stored therein along with the baseline data. Data processor 32 is operable to access the data in cloud 31 and utilize the data to monitor and control poultry environment and health and remedy adverse conditions that are detrimental to the well-being of the poultry flock 61.

The method and apparatus for monitoring poultry in one or more poultry barns has been shown and described in terms of preferred embodiments. Variations and modifications of the apparatus and method can be made by persons skilled in the art without departing from the scope and content of the invention. The apparatus and method for establishing baseline data is applicable to animals confined to an enclosed environment, such as a barn pen or feed lot.

The invention claimed is:

1. An apparatus for establishing baseline data of healthy poultry housed in a poultry barn comprising:
    at least one first sensor device for monitoring and collecting data concerning the temperature and humidity of air outside the poultry barn housing poultry,
    a plurality of second sensor devices for monitoring and collecting data concerning environmental conditions within the barn,
    at least one video device and at least one audio device for monitoring and collecting data concerning the location and concentration of poultry in the barn and the frequencies and intensity of sounds generated by the poultry housed within the barn,
    a cloud for storing data including the data generated by the video device and the audio device,
    a data processor wired to the video, audio and sensor devices operable to process the data from the sensor devices and transfer the processed data to the cloud, and
    a user data processor operable to access the processed data from the cloud to provide baseline data predicated upon the data stored in the cloud including the frequencies and intensity of the sounds generated by the poultry regarding healthy poultry housed within the barn.

2. The apparatus of claim 1 wherein:
    the second sensor devices monitor and collect data including temperature and humidity of the air within the poultry barn, the concentrations of ammonia within the poultry barn and the movement of air within the poultry barn.

3. The apparatus of claim 1 wherein:
    the second sensor devices include at least one sensor device operable to monitor and collect data of the temperature of the air within the poultry barn.

4. The apparatus of claim 1 including:
    a plurality of video devices and audio devices operable to monitor and collect data in different locations in the barn concerning the location and concentration of poultry within the poultry barn and the frequencies and intensity of sounds generated by the poultry housed within the different locations in the poultry barn.

5. The apparatus of claim 4 including:
    at least one sensor device for monitoring and collecting data concerning the temperature and humidity of the air outside the poultry barn housing poultry, and
    said user data processor also being operable to receive the data concerning the temperature and humidity of the air outside the poultry barn housing poultry to add to the baseline data of healthy poultry housed within the poultry barn.

6. The apparatus of claim 4 including:
    at least one sensor device for monitoring and collecting data including temperatures and humidity of the air within the poultry barn and the movement of the air within the poultry barn, and
    said user data processor also being operable to receive the data concerning temperature and humidity of the air within the poultry barn and the movement of the air within the poultry barn to add to the baseline data of healthy poultry housed within the poultry barn.

7. An apparatus for establishing baseline data of healthy poultry housed within a poultry barn comprising:
    at least one audio device located within the poultry barn operable to monitor and collect data concerning the frequencies and intensity of sounds generated by the poultry housed within the poultry barn,
    a cloud for storing the data concerning the frequencies and intensity of sounds generated by the poultry housed within the poultry barn,
    a data processor operable to receive the data from the audio device, process the data and transfer the data to the cloud, and
    a user data processor operable to access data from the cloud and provide baseline data, predicated upon the frequencies and intensity data of sounds generated by the poultry housed within the poultry barn stored in the cloud, of healthy poultry housed within the poultry barn.

8. The apparatus of claim 7 including;
    a plurality of audio devices located in different locations within the poultry barn operable to monitor and collect data concerning the frequencies and intensity of sounds generated by the poultry housed within the poultry barn.

9. The apparatus of claim 7 including:
    a plurality of video devices operable to monitor and collect data in different locations in the barn concerning the location and concentration of the poultry within the barn.

10. The apparatus of claim 7 including:
a plurality of video devices and audio devices operable to monitor and collect data in different locations in the poultry barn concerning the location and concentration of poultry within the poultry barn and the frequencies and intensity of sounds generated by the poultry housed within the different locations in the poultry barn.

11. An apparatus for establishing baseline data of healthy animals housed within an enclosed environment comprising:
at least one audio device located within the enclosed environment operable to monitor and collect data concerning the frequencies and intensity of sounds generated by the animals housed within the enclosed environment,
a cloud for storing the data concerning the frequencies and intensity of sounds generated by the animals housed within the enclosed environment,
a data processor operable to receive the data from the audio device, process the data and transfer the data to the cloud, and
a user data processor operable to access data from the cloud and provide baseline data, predicated upon the frequencies and intensity data of sounds generated by the animals housed within the enclosed environment stored in the cloud, of healthy animals housed within the enclosed environment.

12. The apparatus of claim 11 including;
a plurality of audio devices located in different locations within the enclosed environment operable to monitor and collect data concerning the frequencies and intensity of sounds generated by the animals housed within the enclosed environment.

13. The apparatus of claim 11 including:
at least one sensor device for monitoring and collecting data concerning the temperature and humidity of the air outside the enclosed environment housing animals, and
said user data processor also being operable to receive the data concerning the temperature and humidity of the air outside the enclosed environment housing animals to add to the baseline data of healthy animals housed within the enclosed environment.

14. The apparatus of claim 11 including:
at least one sensor device for monitoring and collecting data including temperatures and humidity of the air within the enclosed environment and the movement of the air within the enclosed environment, and
said user data processor also being operable to receive the data concerning temperature and humidity of the air within the enclosed environment and the movement of the air within the enclosed environment to add to the baseline data of healthy animals housed within the enclosed environment.

15. The apparatus of claim 11 including:
a plurality of video devices operable to monitor and collect data in different locations in the enclosed environment concerning the location and concentration of the animals within the enclosed environment.

16. The apparatus of claim 11 including:
a plurality of video devices and audio devices operable to monitor and collect data in different locations in the enclosed environment concerning the location and concentration of animals within the enclosed environment and the frequencies and intensity of sounds generated by the animals housed within the different locations in the enclosed environment.

* * * * *